(12) United States Patent
Pallaro et al.

(10) Patent No.: US 7,817,183 B2
(45) Date of Patent: Oct. 19, 2010

(54) DETECTION DEVICE TO BE INSTALLED ON A ROAD FOR DETECTING ENVIRONMENTAL CONDITIONS AND MONITORING AND CONTROLLING TRAFFIC

(75) Inventors: Nereo Pallaro, Orbassano (IT); Piermario Repetto, Turin (IT); Filippo Visintainer, Orbassano (IT); Marco Darin, Orbassano (IT); Luca Liotti, Orbassano (IT); Emilio Mosca, Orbassano (IT)

(73) Assignee: CRF Societa Consortile per Azioni, Turin (IT)

( * ) Notice: Subject to any disclaimer, the term of this patent is extended or adjusted under 35 U.S.C. 154(b) by 1150 days.

(21) Appl. No.: 10/939,512

(22) Filed: Sep. 14, 2004

(65) Prior Publication Data
US 2005/0072907 A1    Apr. 7, 2005

(30) Foreign Application Priority Data
Oct. 2, 2003    (IT)    ............ TO2003A0770

(51) Int. Cl.
H04N 7/18    (2006.01)
G08G 1/095    (2006.01)
(52) U.S. Cl. ...................... 348/148; 340/907
(58) Field of Classification Search ............... 348/148; 340/907
See application file for complete search history.

(56) References Cited

U.S. PATENT DOCUMENTS

| | | | |
|---|---|---|---|
| 2,849,701 A | 8/1958 | Clark | |
| 4,023,017 A | 5/1977 | Ceseri | |
| 5,349,267 A | 9/1994 | Brassier et al. | |
| 6,189,808 B1 * | 2/2001 | Daniels et al. | 239/284.2 |
| 6,422,062 B1 * | 7/2002 | King et al. | 73/29.01 |
| 6,812,855 B1 * | 11/2004 | Sudou et al. | 340/907 |
| 2002/0177942 A1 * | 11/2002 | Knaian et al. | 701/117 |
| 2003/0138131 A1 * | 7/2003 | Stam et al. | 382/104 |
| 2004/0141057 A1 * | 7/2004 | Pallaro et al. | 348/148 |

FOREIGN PATENT DOCUMENTS

| | | | |
|---|---|---|---|
| DE | 4200057 A | | 7/1993 |
| DE | 19704818 A | | 8/1997 |
| DE | 19909986 A | | 9/2000 |
| EP | 0 892 280 A | | 1/1999 |
| GB | 2311602 A | * | 10/1997 |
| JP | 7 318 650 A | | 12/1995 |
| WO | 89/02142 A | | 3/1989 |

\* cited by examiner

*Primary Examiner*—Young Lee
*Assistant Examiner*—Richard Torrente
(74) *Attorney, Agent, or Firm*—Sughrue Mion, PLLC

(57) ABSTRACT

A system with a multifunctional integrated visual sensor using a CMOS or CCD technology matrix having a sensitive area divided into Sub-areas dedicated to a series of specific functions.

31 Claims, 8 Drawing Sheets

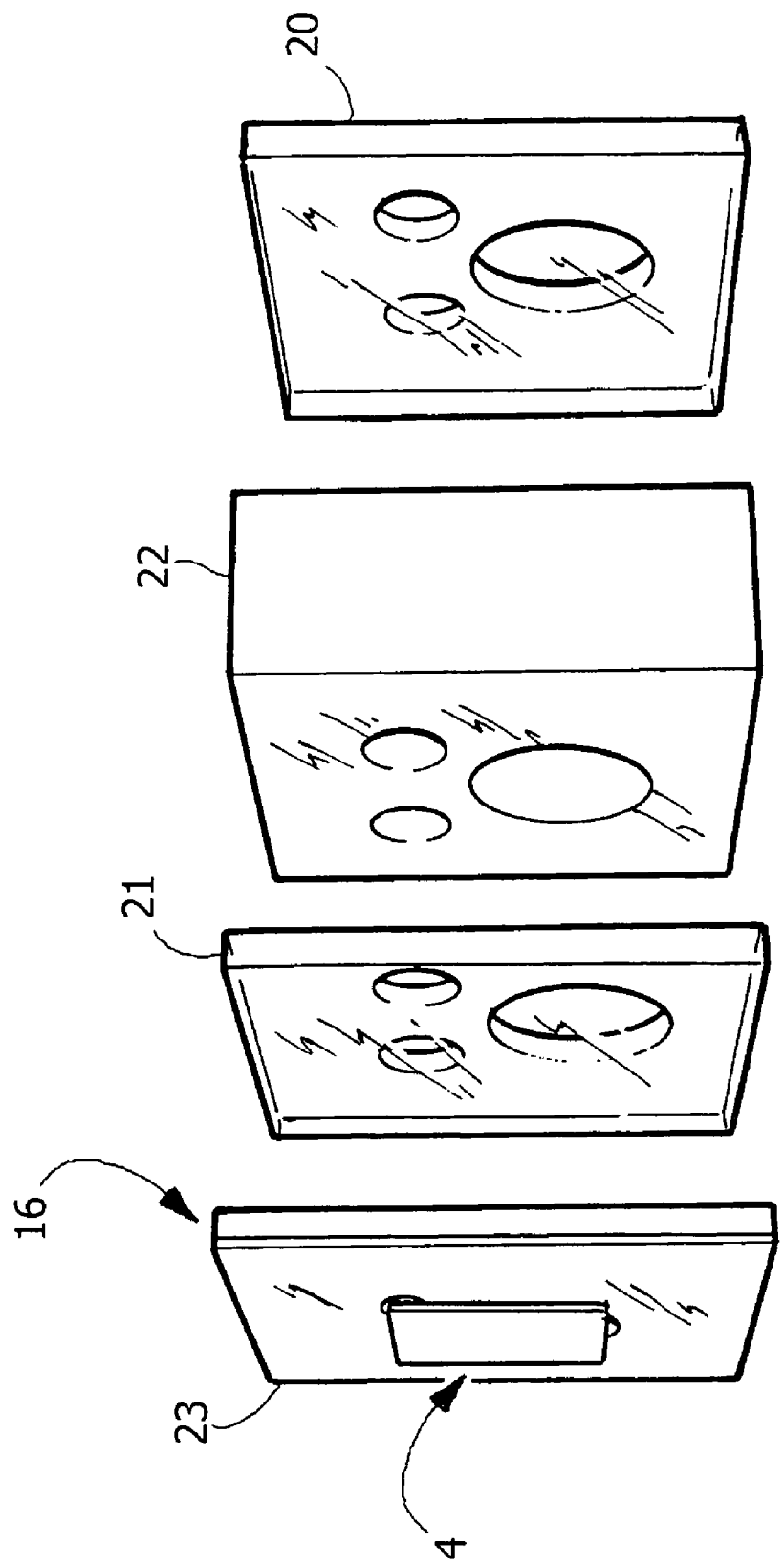

DETECTION DEVICE TO BE INSTALLED ON A ROAD FOR DETECTING ENVIRONMENTAL CONDITIONS AND MONITORING AND CONTROLLING TRAFFIC

REFERENCE TO FOREIGN PRIORITY

This application claims priority to Italian Application No. TO2003A000770, filed on Oct. 2, 2008, the entire application of which is incorporated by reference herein.

BACKGROUND OF THE INVENTION

The present invention relates to the field of stationary detection installations, to be arranged on a road in order to detect and, if necessary, record environmental conditions and to monitor and control traffic.

Already in the past it was deemed as necessary to improve road safety inside and outside towns and cities and on motorways by:
- monitoring environmental and atmospheric conditions (lighting, mist/fog, ice);
- monitoring traffic (number of vehicles traveling in some portions of the road network);
- controlling traffic (queues, accidents, obstacles, violations).

It would be desirable to perform automatically and efficiently said functions, so as to provide users and operators with reliable and real-time information, which allows in particular drivers to modify their driving style (speed, lights on, etc.) or their route (change route or lane) and bodies in charge to modify the concerned installation (lighting, road signs, etc.) and to provide for direct intervention of motorway operators (traffic deviations, aid), as well as to record the scene for after-examination, if required.

In case of fog intermitting emergency lights can be used, with a variable frequency and luminosity, arranged on roads or on traffic dividers. Frequency and intensity of emergency lights, however, should be adjusted depending on outer lighting (day, night, dusk) and visibility conditions so as to obtain an effective signaling and avoid at the same time dazzling phenomena.

The Applicant does not know about prior solutions in the field referred to above, providing for a visual sensor for road applications integrating several functions into its sensitive area.

Conversely, known solutions concern:
- sensors for measuring visibility (U.S. Pat. No. 4,931,767, EP0635731B1, GB2224175A, DE19749397, EP0691534, U.S. Pat. No. 5,118,180, U.S. Pat. No. 5,206,698, WO8909015A1, U.S. Pat. No. 5,987,152, DE29811086, U.S. Pat. No. 4,502,782, FR 2745 915)
- stationary positions for traffic control (U.S. Pat. No. 5,777,1484, GB2288900, IT MI93A001604, EP1176 570, FR2771363)

SUMMARY OF THE INVENTION

The main aim of the present invention is therefore to suggest a detection device based on a multifunctional visual sensor for monitoring and controlling traffic and for detecting fog/visibility, to be installed on a road or motorway portion (for instance on portals), which is simple, compact, cheap and highly reliable.

A further aim of the invention is to suggest a system as referred to above, which can also be used on a control vehicle (for instance a safety car), for dynamically monitoring environmental and traffic conditions on a motorway.

In the light of achieving said aim, the object of the invention is a detection device having the characteristics as listed in claim 1.

Further advantageous characteristics concerning preferred embodiments of the invention are listed in the dependent claims.

In the preferred embodiment of the invention, the aforesaid functions are integrated into a CCD or CMOS matrix by dividing its sensitive area.

Visibility detection becomes much "stronger" by combining active techniques (indirect, local and accurate measuring) with passive techniques (direct, extended and self-assured measuring).

Visibility detection with active technique is based on an indirect measuring: what is detected is the backscattering radiation connected to fog density in the concerned volume. This is a simple, accurate and widely tested method. However, it is characterized by some disadvantages, i.e. it is a local (evaluation of fog density close to the sensor) and indirect measuring (correlation between fog density and visibility through half-empirical formulas).

Conversely, visibility detection with passive technique is based on a direct measuring of visibility over an extended area (fog evaluation in the space or scene before the sensor, by measuring light intensity and/or contrast) and enables to detect also the presence of a fog bank (or any other particle suspension compromising visibility, such as smoke) starting at a given distance (up to 50-100 m) from the sensor.

With suitable data fusion algorithms, based on the comparison between signals collected with both techniques and the use, if necessary, of environmental lighting, humidity and temperature data, it is possible to exploit the advantages of both techniques and obtain an accurate and self-assured evaluation of visibility, which also takes into account detection conditions (day/night), and which can predict, if necessary, fog formation and/or thinning out.

The portion of the sensitive area of the matrix dedicated to passive fog detection also performs functions of traffic monitoring and control.

The device also integrates a temperature and relative humidity sensor, from which dew temperature can be obtained, which parameters can be useful in case of use of a mathematic model for predicting possible fog formation.

Lighting detection, together with visibility evaluation, becomes strictly necessary in order to modulate the intensity and/or adjust the frequency of emergency lights on the concerned road portion, so as to make said lights well visible to vehicles, however avoiding dangerous phenomena of drivers' dazzling.

The advantages offered by this kind of approach are therefore:
1. integration of several functions necessary for the application context;
2. prediction on possible fog formation, presence of fog banks and more self-assured visibility detection;
3. compact and simple system, cost reduction

BRIEF DESCRIPTION OF THE DRAWINGS

The present invention shall now be described in detail with reference to the accompanying drawings, given as a mere non-limiting example, in which:

FIG. 8 shows a magnified exploded perspective view of a detail of FIG. 7.

DETAILED DESCRIPTION OF THE INVENTION

The integrated visual system for road applications is characterized by the following functions or a part thereof:
- detection of visibility level (in meters) related to the presence of mist or fog;
- detection of fog banks;
- detection of environmental lighting level (in lux);
- detection of inner and outer temperature;
- detection of outer relative humidity;
- traffic monitoring;
- traffic control;
- self-adjustment because of partially dirty optical window, sensor temperature variation and power reduction of emitters;
- self-cleaning optical window or window cleaning;
- wireless data transmission with bridge connection between identical or lower function sensors;
- self-diagnosis.

The system architecture consists of:
- CCD or CMOS visual sensor (standard or dedicated with pixel level pre-processing);
- temperature sensor;
- relative humidity sensor;
- emitter for visibility detection with passive technique;
- optical receiving (for radiation collection and focusing on different matrix areas) and transmitting (for shaping emitting bundle) system;
- mechanical system for lining up optical systems and separating areas dedicated to different functions;
- electronic system for acquiring and processing images, emitter control, acquisition of temperature and humidity signal, wireless transmission, self-diagnosis.

The system can be installed for instance on portals present on motorways, so as to monitor a relevant road portion.

Figure 1:
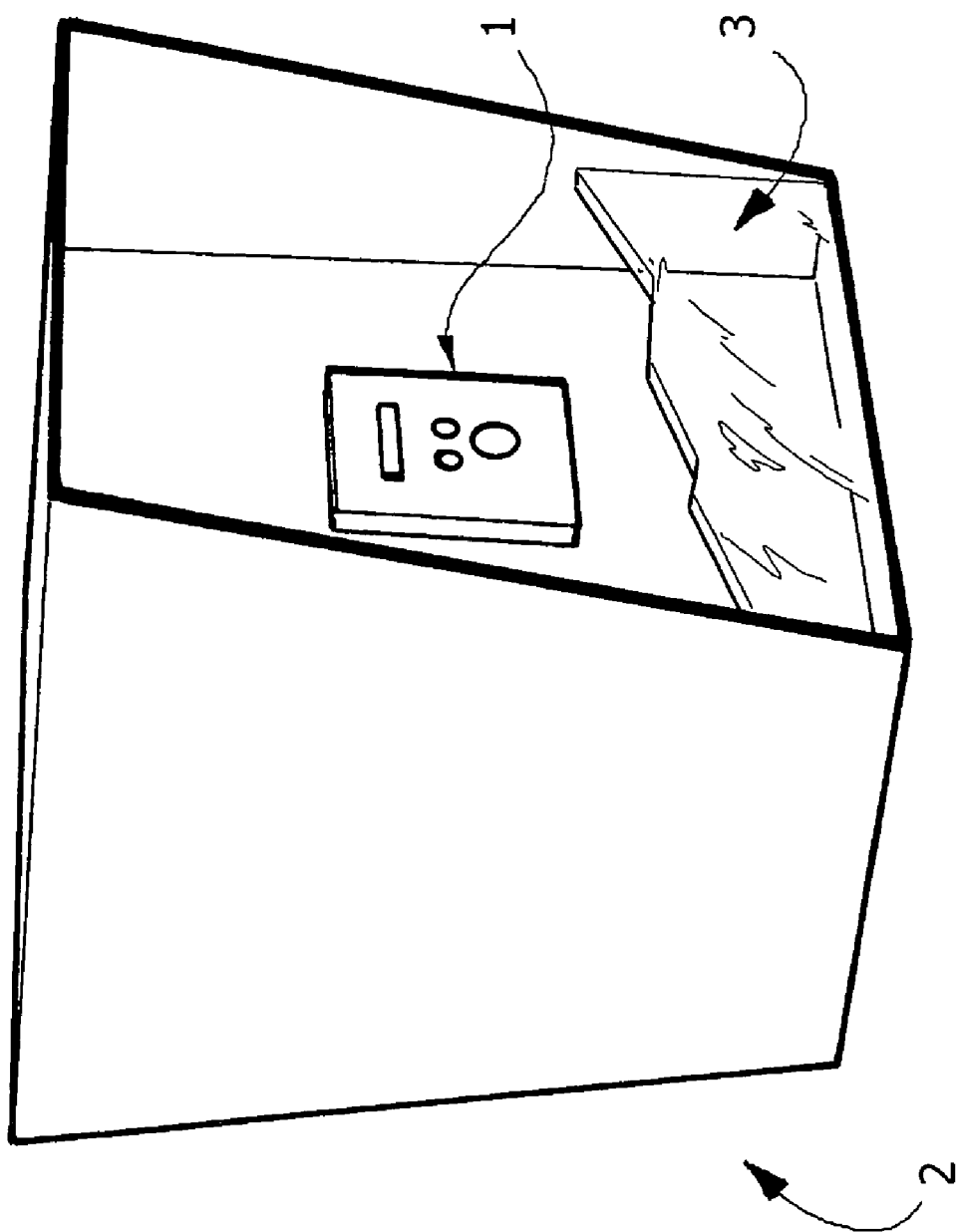
FIG. 1 is a view of the device, the multifunctional sensor being integrated into a sealed box with wings so as to reduce the impact of atmospheric agents onto the optical window.

FIG. 1 of the accompanying drawings shows an example of embodiment of the outer shell 2 of the device, having a front surface with an area 1 in which the real detection system (which shall be described in detail in the following) is placed, protected by an optical window 3.

This invention draws on the proposal constituting the object of claim 1 of Italian patent application T02002A000950, filed on 05.11.2002 and still undisclosed at the priority date of the present invention. The whole content of the aforesaid patent application is included herein as a reference. However, it should be pointed out that the aforesaid invention related to a non-stationary visual system, installed on a vehicle and comprising a CCD or CMOS matrix having a sensitive area divided into sub-areas, each designed for a specific function in scene monitoring or in the detection of environmental parameters, said division being obtained by means of optical systems (imaging systems and not), having different directions and/or fields of view and/or optical separation modes of said sub-areas.

Figure 2:
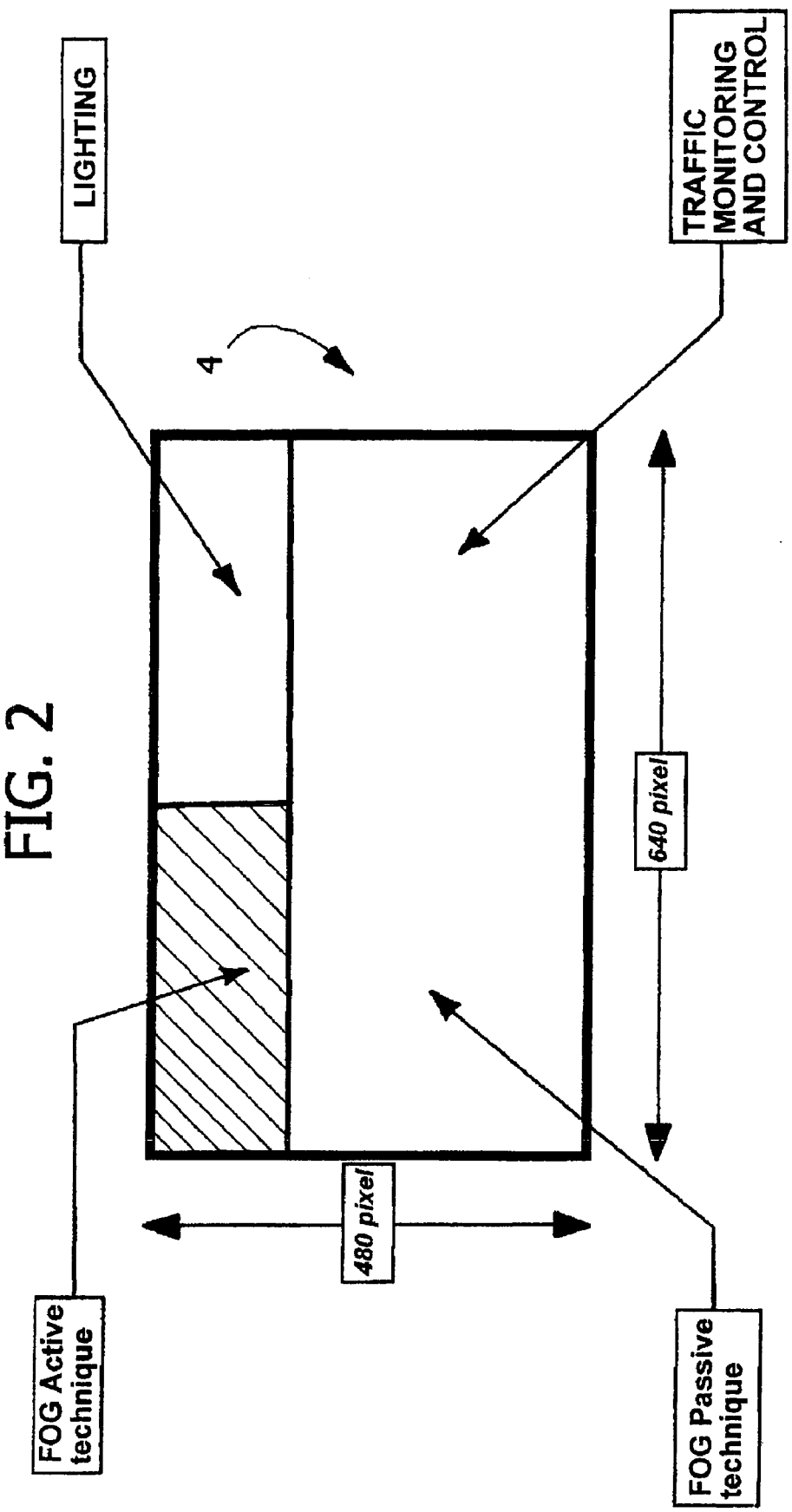
FIG. 2 is a schematic view of a first embodiment of the matrix sensor according to the invention, which implements some of the functions discussed above.

As can be seen in FIG. 2, the sensitive area of the matrix 4 of the new system according to the present invention is divided into sub-areas whose number, position and size differ from the content of the aforesaid patent application. In the arrangement of FIG. 2, the matrix 4 has its sensitive area divided into specific sub-areas dedicated to the following functions:

1. traffic monitoring and control, visibility (passive technique), fog banks;
2. visibility (active technique);
3. environmental lighting.

Moreover, the following further functions can be provided for:

4. dirt on optical window (active or passive technique);
5. operation/monitoring of optical power of emitters.

Fog lowers visual efficiency since it reduces environmental contrast and therefore visible space, sometimes up to few meters. Basically, visual efficiency gets worse because of the lower depth perception, which is absolutely necessary to check and evaluate the position of objects in space.

The visibility function is performed by combining two sub-areas: in the first one, the backscattering radiation generated by the presence of fog, which is related to visibility level, is measured with an active technique (i.e. via an emitter, for instance a LED or a laser diode); in the second sub-area, which coincides with the sub-area dedicated to traffic monitoring and control, road or motorway scene is acquired with a passive technique, and by means of algorithms of different type and complexity (e.g. contrast analysis; evaluation of parameters such as shading, ratio to horizon, overlapping, parallax, etc.) the presence of fog banks is detected, thus obtaining an evaluation on non-local visibility.

Figure 3:
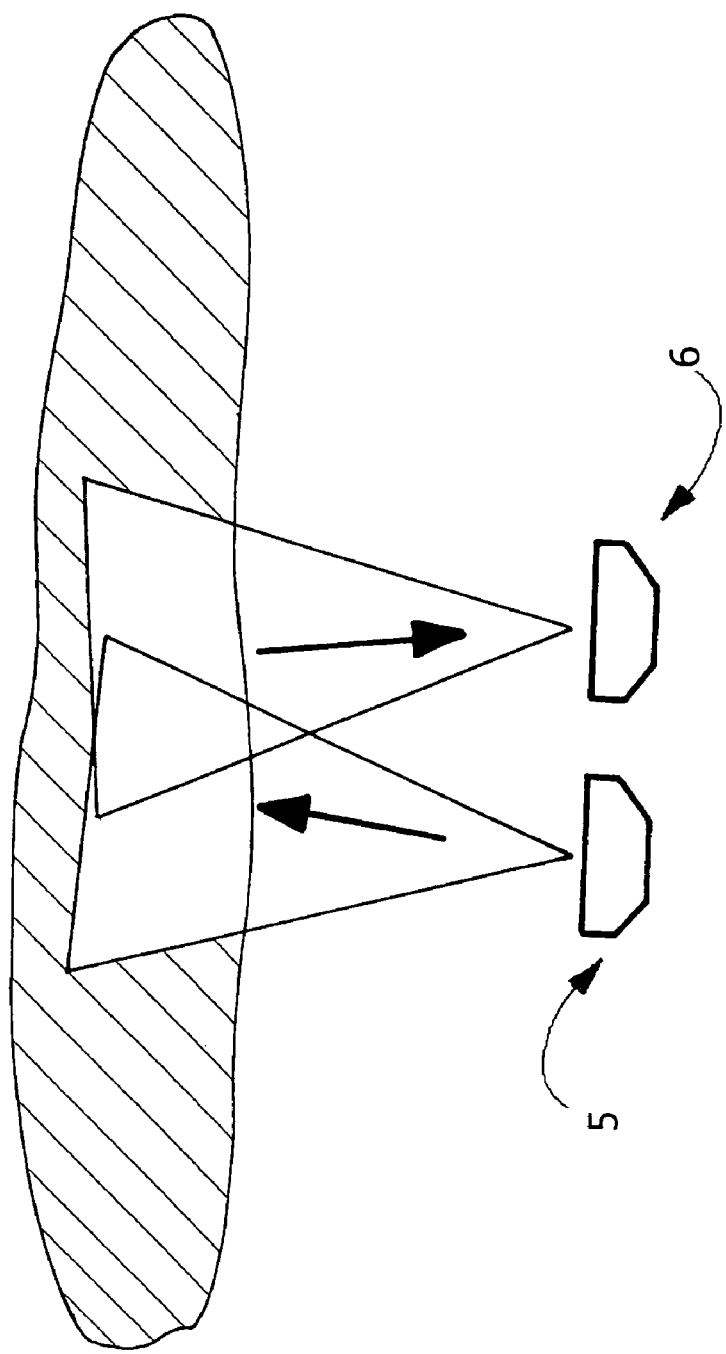
FIG. 3 is a principle diagram of active fog detection.

FIG. 3 shows schematically the principle of fog detection with active technique. In this figure numbers 5 and 6 refer to emitter and receiver, respectively.

In a possible arrangement, the area dedicated to traffic monitoring gives, beyond the number of vehicles traveling in some portions of the road network, also the type of flow (cars instead of trucks; average speed of traveling vehicles in case of queues) thanks to accurate image processing analyses. In the meantime parameters that are useful for traffic control are measured, such as: speed (both for cars and trucks), safety distance, emergency lane occupied, queues, accidents.

The function of environmental lighting is performed by a specific sub-area of the matrix or by a sub-area contained in the one dedicated to traffic monitoring.

The function of dirt on optical window can be performed both with an active technique, i.e. with an emitter, and with a passive technique, i.e. without emitter, and can use as sensitive area a sub-area of the CMOS matrix or a separate receiving module.

In a possible arrangement, the system is equipped with an electro-optical emitting-receiving module separated from the visual matrix (though integrated into the sensor), so as to perform in an active manner the function of dirt on optical window.

According to a further preferred feature of the invention, the function of dirt on optical window is performed in an active manner (i.e. via an emitter), but the receiver is said visual matrix, with a sub-area dedicated to said function or with a sub-area contained in the one dedicated to one of the aforesaid functions.

Still according to a preferred feature of the invention, the function of dirt on optical window is performed with a passive technique (for instance image analysis) in a matrix sub-area dedicated to said function, or in a sub-area contained in the one dedicated to one of the aforesaid functions (for instance the sub-area dedicated to scene monitoring).

The monitoring of emitted optical power is performed through a sub-area dedicated to said function or by means of a photosensitive detector separated from the matrix or by means of an electronic circuit monitoring control current and environmental temperature.

In a possible arrangement, the system is further equipped with a sensor for measuring camera temperature (for instance a thermocouple or a PCB temperature sensor), so as to compensate matrix response when temperature varies in those functions requiring an absolute value as output.

In a possible arrangement, the system is further equipped with a sensor for measuring outer temperature (for instance a thermocouple) and outer relative humidity so as to obtain dew temperature; these parameters enable to predict fog formation.

The optical system enabling an integration of traffic monitoring, lighting and fog functions onto the same CMOS matrix can be carried out in accordance with two different arrangements:

1. Arrangement with Standard Optical Elements (FIG. 6)

Figure 5:
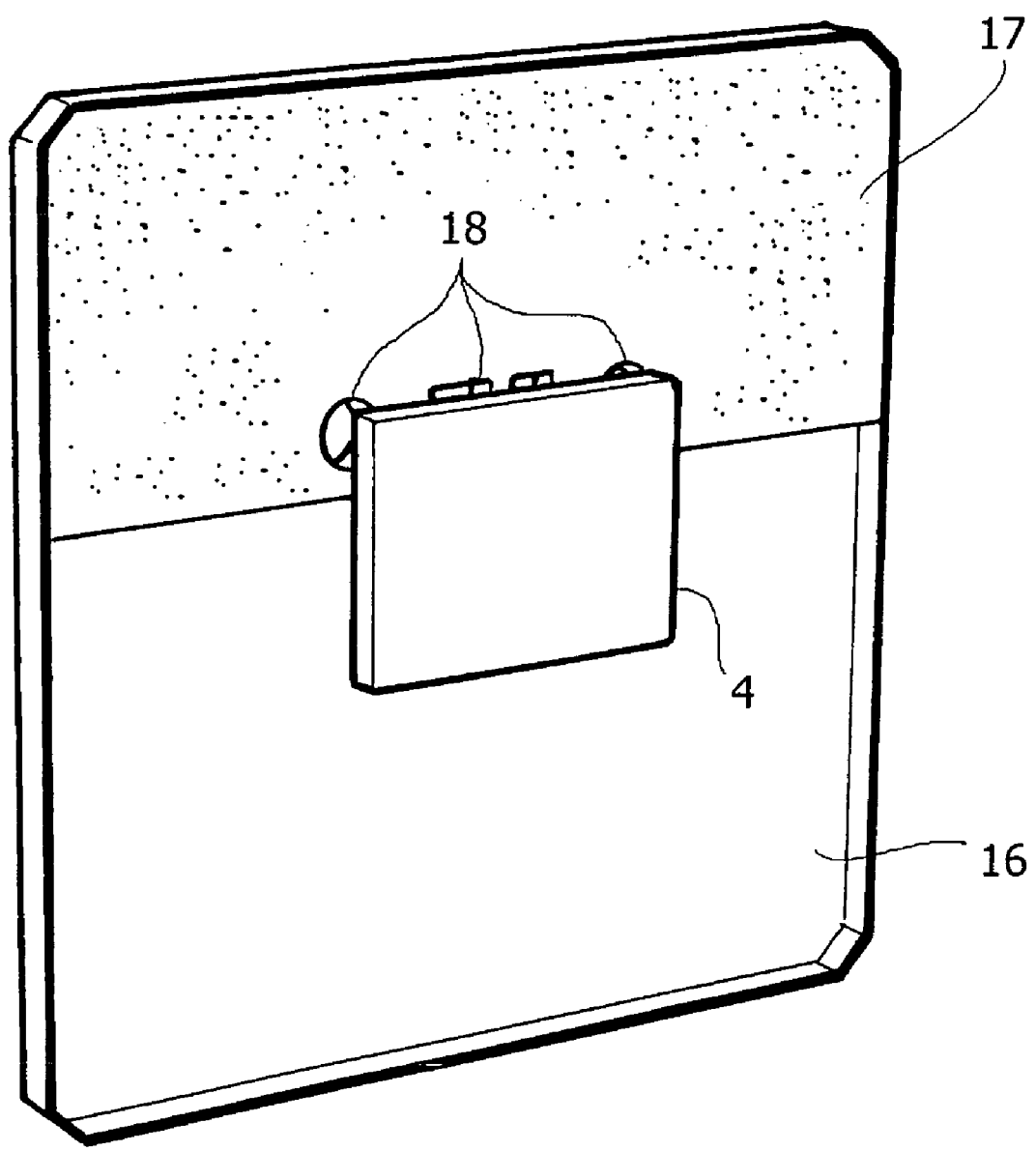
FIG. 5 shows a perspective view of the assembly comprising the sensor matrix according to the invention with the protection window associated thereto.
Figure 6:
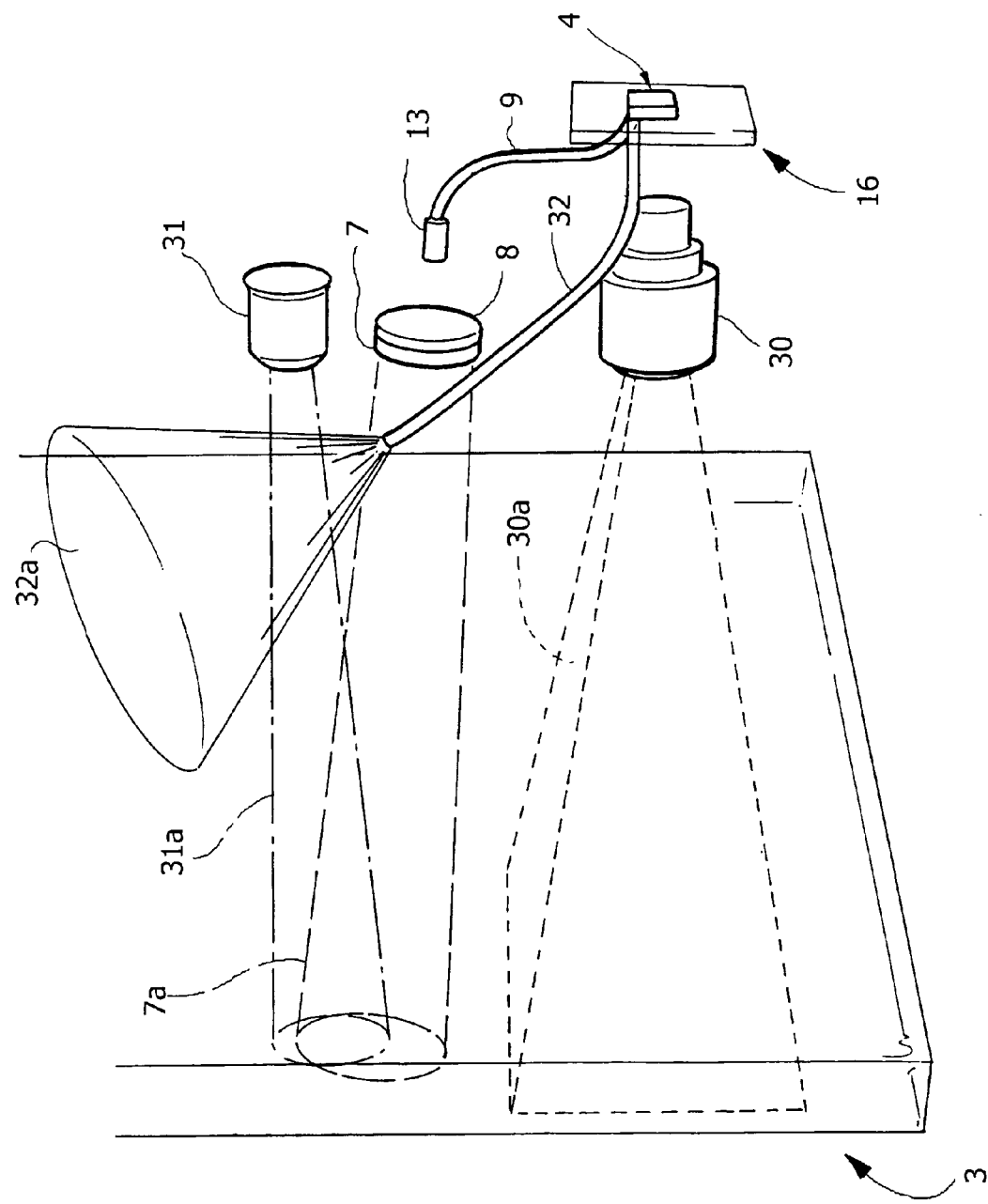
FIG. 6 is a schematic perspective view of the various elements constituting a first embodiment of the device according to the invention.

With reference to the embodiment shown in FIG. 6, scene monitoring function includes an objective 30 (for instance a microvideo lens, with a diameter of 12 mm and a length of 20 mm approximately) with a suitable focal length (for instance f=6 mm) and with an optical axis inclined with respect to road plane so as to frame a road portion, shifted with respect to matrix center and orthogonal to matrix plane. The matrix 4 with its protection glass 16, having an opaque area 17 and openings 18, is placed behind the objective (see also FIG. 5).

For passive technique fog function the same objective as for scene monitoring is used.

According to a preferred feature, the imaging optical system for performing scene monitoring and passive fog detection consists of a dedicated system based on micro-optical components.

Figure 4:
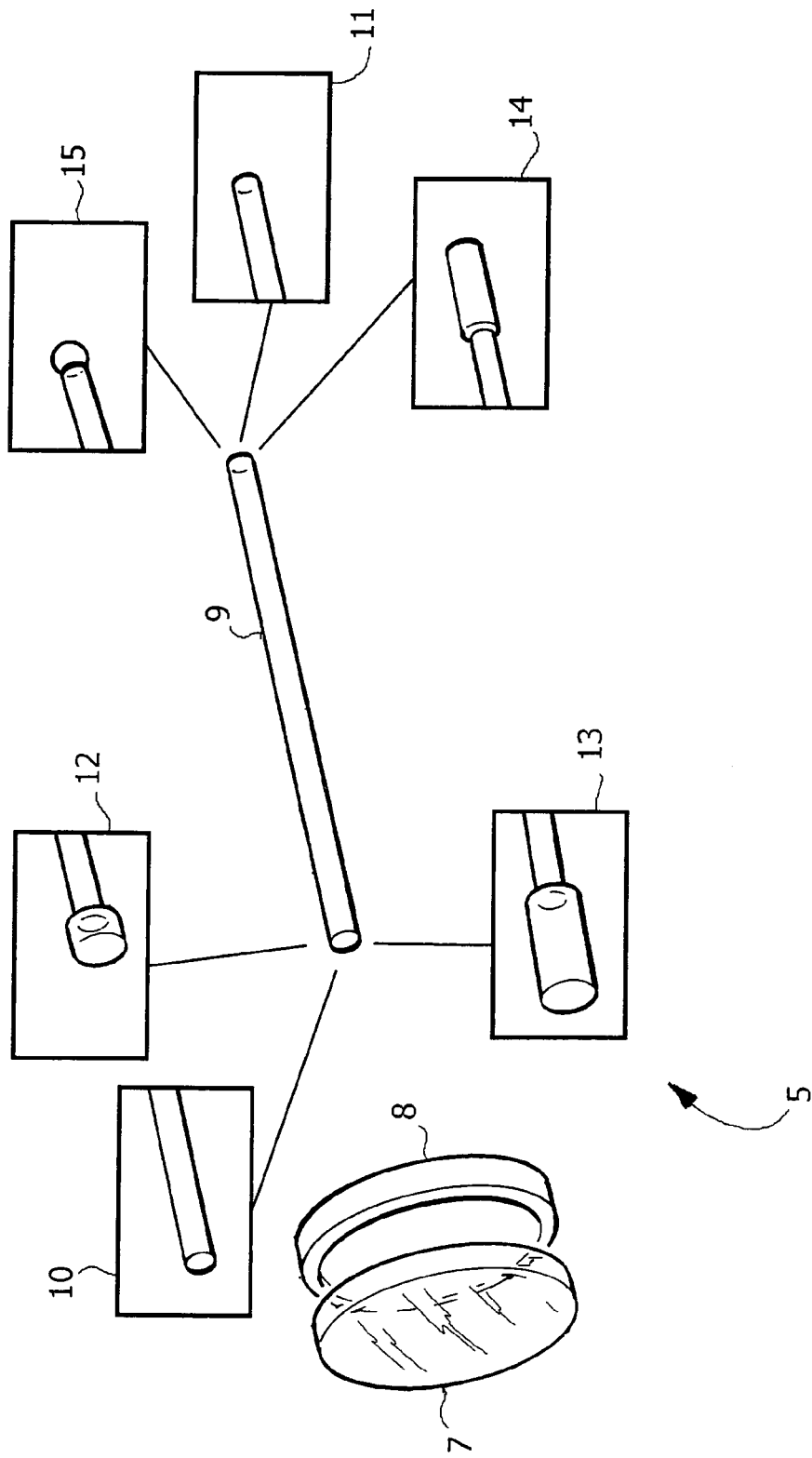
FIG. 4 shows possible execution variants of the optical receiving system for fog detection.

For active technique fog function a glass or plastic optical fiber 9 (see also FIG. 4) is used, having an end close to the matrix 4, provided with a ball lens 15 or a GRIN (gradient of index) lens 15, or also with no lens at all (as in 11), and a front end provided with a GRIN lens 13 or with a micro-optical component, or also with no lens at all (as in 10). The front end of the optical fiber 9 is associated to a high-pass (transparent at wavelengths above 800 nm)/interferential filter 8, which could also be absent, and to a collection lens 7, which can be a collection lens without filter or a collection lens with high-pass material with interferential coating.

Optical fibers are a cheap and compact solution for modifying the direction of the field of view with respect to the direction orthogonal to the matrix. As a matter of fact, since in backscattering technique the presence of obstacles can jeopardize the correctness of visibility measuring, the field of view of the receiver should preferably be oriented in the direction of horizon or some degrees upwards.

The collection lens 7 aims at focusing onto the optical fiber the incident radiation within a field of view of 7-8°. Preferably, an anti-reflection coating should be applied onto the collection lens.

The high-pass/interferential filter 8 aims at limiting the disturbance due to environmental light, filtering only radiation components in a band adjusted to the wavelength of the emitter (800-900 nm).

According to a preferred feature, the collection lens 7 can act as an optical band-pass filter, being made of a high-pass material, onto which a suitable interferential coating is laid, so that the spectral passing window is adjusted to the wavelength of the emitter.

The use of microlenses or GRIN lenses upstream or downstream from the optical fiber can improve fiber coupling efficiency and focusing onto CMOS matrix, respectively. In the latter case, not only is there an intensity gain, but also radiation spot onto the matrix is reduced.

Another solution for filtering the signal of the emitter (referred to with number 31 in FIG. 6) consists in using as emitter a LED modulated to a given frequency and an electronic band-pass filtering system at the frequency of the emitter. This solution is alternative or complementary to the use of the optical filter.

A further solution for filtering the signal of the emitter 31 consists in using the environmental lighting signal to calculate background intensity and subtracting the latter from the signal of the fog detector. This solution is alternative to the filtering systems already described.

For lighting function an optical fiber 32 made of plastic or glass for collecting light is used, as in the case of passive technique fog function. No collection lens should however be used, since the detected signal has a sufficient intensity.

Lighting function can also be carried out by calculating the average incident intensity on the area dedicated to traffic monitoring or to passive fog detection. In such case the same optical component as in these functions can be used.

For active technique dirtying function an optical system as the one of active technique fog function is used. In such case, however, the fields of view of emitter and receiver overlap in a smaller volume, including a portion of the optical window. The optical system related to this function can thus make use of one or more components among those listed for active technique fog function. If radiation is filtered electronically, a modulation frequency differing from the one used for fog function should preferably be used.

For passive technique dirtying function the same objective as for scene monitoring is used.

In FIG. 6 number 30a, 7a, 31a, 32a refer to, respectively, the fields of view of the objective 30, of the lens 7, of the emitter 31 and of the optical fiber 32.

2. Arrangement with Micro-Optical Components (FIGS. 7, 8)

Figure 7:
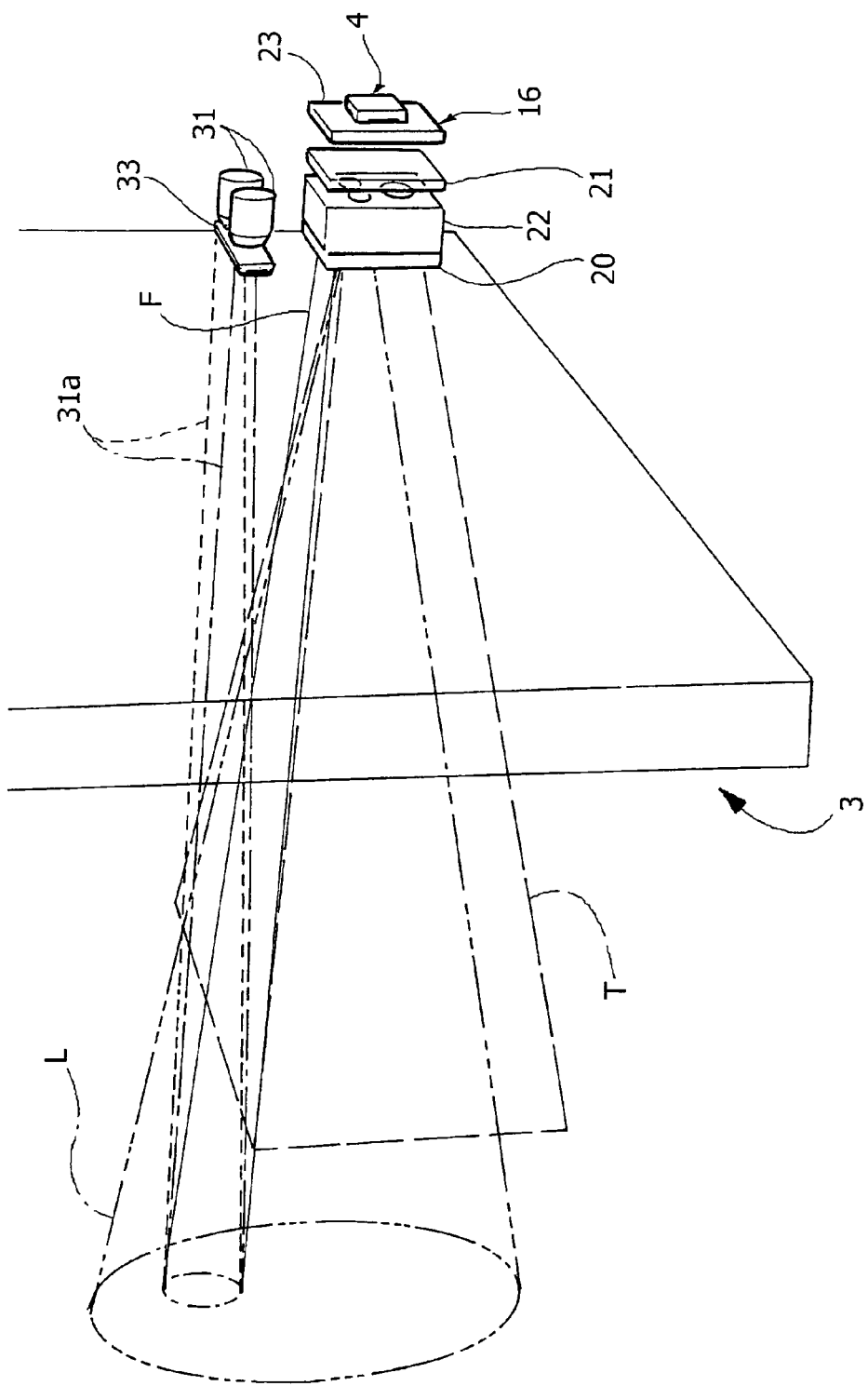
FIG. 7 shows a schematic perspective view of the various elements constituting a second embodiment of the device according to the invention, based on microoptical systems whose components are camera sensitive area, field stop, microlens matrix, optical insulation, microlens matrix.

In the case of the second embodiment shown in FIG. 7, 8, the optical collection components for the previous functions are systems including microlenses or microlenses-prims-microlenses.

The system can consist or one or more matrixes of microlenses, arranged before the CMOS matrix. One or more microlenses can be present on each matrix. In the case shown (see FIG. 8), it is provided for a matrix 21 of micro-optical components close to the sensor 4, and a matrix 20 of micro-optical components arranged towards the outside of the device.

For each function the optical system consists of one or more microlenses placed on different matrixes.

The problem involving the direction of the optical axis can be solved in two ways:

1. use of micro-mirrors or micro-prisms (wedge-type or total reflection);
2. axial shift or tilt of micro-lenses.

The global optical chain can also comprise matrixes of microfilters, or simply optical windows partially covered with an interferential coating.

In order to insulate and adjust the diaphragm of the optical system for each function, one or more substrates of absorbing material, conveniently perforated, can be used. Depending on their position in the optical chain (before or after microlens matrixes), these substrates can act as aperture stop, as stray light baffle or as field stop. In the latter case, it is preferable to use not a stand-alone substrate but an absorbing coating, laid onto the optical protection window of the CMOS matrix. In case shown (see FIG. 8) it is provided for an optical insulation element 22 with aperture stop, placed between the two micro-optical matrixes, and an element 23 close to the sensor 4, acting as field stop.

In the optical chain related to each function, the prism deviates the optical axis (in case active fog and lighting functions are to be oriented upwards), whereas the microlens (or microlenses) focuses the transmitted optical signal.

Still according to the invention, the sensor is also provided with a protection window 16, made of glass or transparent plastic material, which also acts as a support for optical fibers (for the arrangement with standard optical elements) and, if necessary, with a prism; these optical components are inserted into holes made in said window.

According to a preferred feature, the protection window coincides with the substrate onto which the microlens matrix close to the photosensitive area is laid.

With reference to FIG. 7, the latter shows two LEDs 31 acting as emitters to which a beam shaping lens 33 is associated. References 31a, L, F, T symbolize, respectively, the emission lobes of the LEDs 31, the field of view for lighting function, the field of view for active technique fog function and the field of view for traffic monitoring and control.

Still according to a further feature of the invention, an optical insulation system is placed between the areas of the CMOS matrix dedicated to the various functions, which system consists of a partial coating of the surface of the matrix protection window, on the side towards the matrix, with a layer of absorbing or reflecting material, for instance by serigraphy or thermal evaporation. In case prisms are used, also prism faces should be partially coated with a layer of absorbing or reflecting material, for instance by serigraphy or thermal evaporation.

In the arrangement with microlenses, the optical protection window can be a microlens matrix, with no limitation concerning the laying of the absorbing coating.

The visual sensor can be a CCD or CMOS sensor, with a different size depending on the number of performed functions and on the field of view designed for traffic monitoring and control.

According to a preferred feature, the CMOS sensor has a logarithmic response so as to have an almost linear development of visibility (in meters) depending on pixel light intensity, and thus a higher resolution for levels of visibility above 100 m.

According to a preferred feature, the color CMOS sensor can improve the strength of visibility evaluation algorithm; RGB levels in case of fog get saturated, thus making the image less brilliant and tending to white.

Image acquisition can be complete on the whole matrix (in case of CCD) or limited to matrix sub-areas (in case of CMOS). The second option enables to use different parameters and acquisition speeds for each sub-area.

In active fog function, beyond the optical signal filter, there is a further filtering system, based on signal acquisition together with the emitter (for instance in windowing mode the signal originating from the dedicated sub-area is acquired with a frame rate at least twice the frequency of radiation source), and on the use of suitable digital filters.

The device is further equipped with an integrated electronic module, for signal acquisition and processing, and with a wireless data transmitting-receiving module, for communication with other identical or lower function sensors.

For the functions of visibility measuring with active and passive technique, the electronic module can compare the signals related to both types of measuring, and use in addition, if necessary, the environmental lighting signal, so as to give as output—through suitable algorithms—an accurate and self-assured visibility signal.

According to a further preferred feature, the electronic module also uses temperature and humidity signals for evaluating visibility, in a data fusion algorithm improved with respect to the previous one, and predicting, if required, fog formation and thinning out.

In view of an application in the field of telecommunications, it might be possible to:

1) use each sensor as a bridge for data transmission from one sensor to the other: each sensor receives data from the preceding sensor and transmits them to the following one, and conversely. This transmission goes on as far as a base station, which uses the received information for processing warning messages, alternative routes, for calling the police, etc.

2) use all or part of the sensors for transmitting instructions-information to oncoming vehicles.

The base station can simultaneously connect via GSM/GPRS/UMTS to a central database for uploading data concerning a given road portion, and also for downloading information to be transmitted to traveling vehicles.

What is claimed is:

1. Stationary detection device to be installed on a road for detecting environmental conditions and monitoring and controlling traffic, said stationary device comprising:

sensor means including a CCD or CMOS matrix of optical sensors defining a sensitive area, said sensitive area being divided into a plurality of sub-areas, and a plurality of different optical systems respectively associated to a different ones of said different sub-areas of the sensor matrix, corresponding to different directions and/or fields of view by which the scene is seen by said different optical systems, so that different sub-areas carry-out different specific monitoring functions simultaneously, wherein at least a first sub-area and a respective first optical system monitor the traffic of the vehicles traveling along a road by observing queues of vehicles, accidents, obstacles or violations, whilst at least a second sub-area and a respective second optical system detect the presence of mist, fog and fog banks, and at least a third sub-area and a respective third optical system detect lighting; and wherein the second optical system includes an emitter and receiver for respectively emitting and receiving an optical signal;

wherein the third sub-area of the sensor matrix dedicated to the lighting detection function is used to actuate a corresponding adjustment of emergency lights along a portion of the road wherein said stationary detection device has an optical window and wherein one of said sub-area of the sensor matrix is dedicated to detection of dirt on said optical window.

2. Detection device according to claim 1, wherein the detection device is installed on a series of portals placed at a given distance one from the other on a road portion.

3. Detection device according to claim 1, wherein said sensor means integrate the function of fog bank detection.

4. Detection device according to claim 1, wherein said sensor means integrate inner temperature detection for the self-adjustment of the response of sensor means.

5. Detection device according to claim 1, wherein said sensor means integrate a self-adjusting function as a result of partially dirty optical window, sensor temperature variation and power reduction of emitters.

6. Detection device according to claim 1, wherein said sensor means comprise a self-cleaning optical window or means for cleaning the latter.

7. Detection device according to claim 1, wherein the detection of dirt on optical window is performed in an active mode via an emitter.

8. Detection device according to claim 1, wherein the detection of dirt on optical window is performed in an active mode, including a receiver which is a visual matrix, with a sub-area dedicated to said function or with a sub-area contained in the one dedicated to one of the other functions.

9. Detection device according to claim 1, wherein the detection of dirt on optical window is performed in a passive mode, in a matrix sub-area dedicated to said function or in a sub-area contained in the one dedicated to one of the aforesaid functions.

10. Detection device according to claim 1, wherein the monitoring of emitter operation includes monitoring the emitted optical power through a sub-area dedicated to said function or through a photosensitive detector separated from the matrix or through an electronic circuit monitoring control current and environmental temperature.

11. Detection device according to claim 1, wherein the sub-area dedicated to scene monitoring and passive fog detection uses an objective with a convenient focal length, placed at a distance from matrix center.

12. Detection device according to claim 1, wherein the sub-area dedicated to scene monitoring and passive fog detection receives the optical signal through a system of microlenses.

13. Detection device according to claim 1, wherein the sub-area dedicated to fog function based on active technique receives the optical signal through a ball or GRIN (gradient of index) lens, or also no lens at all, in association with a glass or plastic optical fiber, if necessary with another GRIN or micro-optical lens, or also with no lens at all, in association with a high-pass/interferential filter 8, which could how ever also be absent, with a collection lens without filter or a collection lens provided with high-pass material with interferential coating.

14. Detection device according to claim 13, wherein in order to filter the disturbance deriving from environmental lighting, in addition or as an alternative to the optical filter, a LED modulated to a given frequency and an electronic bandpass filtering system at emitter frequency are used as emitter.

15. Detection device according to claim 13, wherein in order to filter the disturbance deriving from environmental lighting, the environmental lighting signal is used for calculating background intensity and subtracting it from fog detector signal.

16. Detection device according to claim 1, wherein in the sub-area dedicated to lighting function the optical signal is collected by means of an optical fiber made of plastic or glass.

17. Detection device according to claim 1, wherein optical collection components for the various functions consist of one or more matrixes of overlapping microlenses or microlenses-prisms-microlenses, whereby one or more microlenses can be present on each matrix, and for each function the optical system comprises one or more microlenses arranged on different matrixes.

18. Detection device according to claim 1, wherein an optical axis can be oriented by using micro-mirrors/micro-prisms or by axial shift or tilt of micro-lenses.

19. Detection device according to claim 1, wherein in order to insulate and adjust the diaphragm of the optical system for each function, one or more substrates of absorbing material, conveniently perforated, are used, said substrates being placed before or after microlens matrixes so as to act as aperture stop, as stray light baffle or as field stop.

20. Detection device according to claim 1, wherein the sensor means have a protection window made of glass or transparent plastic, also acting as support for optical fibers (in the arrangement with standard optical elements) and, if necessary, a prism, which optical components are inserted into holes made in said window.

21. Detection device according to claim 20, wherein the protection window made of transparent plastic coincides with the substrate onto which a microlens matrix close to the photosensitive area is laid.

22. Detection device according to claim 1, wherein the detection device is provided for an optical insulation system between the areas dedicated to the various functions, based on a partial covering of the surface of the matrix protection window or of a microlens matrix, on the side towards the matrix, with a layer of absorbing or reflecting material by serigraphy or thermal evaporation.

23. Detection device according to claim 1, wherein the matrix is a CCD or CMOS matrix, with a different size as a function of the number of performed functions and of the field of view designed for traffic monitoring and control.

24. Detection device according to claim 1, wherein the CMOS sensor has a logarithmic response so as to have an almost linear development of visibility as a function of pixel light intensity, and thus a higher resolution for levels of visibility above 100 m.

25. Detection device according to claim 1, wherein the CMOS sensor is a color sensor so as to strengthen the algorithm of visibility evaluation with passive technique; RGB levels in case of fog get saturated, thus making the image less brilliant and tending to white.

26. Detection device according to claim 1, wherein the matrix is a standard or parallel architecture (pixel pre-processing) CMOS matrix.

27. Detection device according to claim 13, wherein in active fog function, beyond the optical signal filter, there is a further filtering system, based on signal acquisition together with the emitter and on the use of suitable digital filters.

28. Detection device according to claim 1, wherein visibility is evaluated by an electronic module by comparing the signals originating from active and passive technique fog functions, adding when necessary the environmental lighting signal; evaluation takes place through such suitable algorithms as to give as output an accurate and self-assured visibility signal.

29. Detection device according to claim 1, wherein an electronic module also uses temperature and humidity signals for evaluating visibility, in a data fusion algorithm improved with respect to the previous one, and predicting fog formation and/or thinning out.

30. Detection device according to claim 1, wherein said sensor means further comprise a wireless data transmitting-receiving module for communication with other identical or lower function sensors: each sensor receives data from the preceding sensor and transmits them to the following one, and conversely; transmission goes on as far as a base station.

31. Detection station according to claim 1, wherein said sensor means are used at least partly for transmitting instructions-information to oncoming vehicles.

* * * * *